United States Patent [19]

Utsunomiya et al.

[11] Patent Number: 5,641,884

[45] Date of Patent: Jun. 24, 1997

[54] SPIRO-NAPHTHO-OXAZINE COMPOUND AND PHOTOSENSITIVE MATERIALS USING THE SAME

[75] Inventors: Akira Utsunomiya; Shinichi Sato; Hiroyoshi Yamaga; Nobuo Suzuki, all of Tokyo, Japan

[73] Assignee: Hodogaya Chemical Co., Ltd., Tokyo, Japan

[21] Appl. No.: 363,836

[22] Filed: Dec. 27, 1994

[30] Foreign Application Priority Data

Dec. 28, 1993 [JP] Japan ................................ 5-349088
Sep. 28, 1994 [JP] Japan ................................ 6-257298

[51] Int. Cl.$^6$ .................... C07D 413/14; C07D 413/04
[52] U.S. Cl. .................... 544/71; 252/586; 359/885; 544/58.6
[58] Field of Search .................... 544/71; 354/354

[56] References Cited

U.S. PATENT DOCUMENTS

| 4,913,544 | 4/1990 | Rickwood et al. ............... 544/71 |
| 5,180,524 | 1/1993 | Casilli et al. ............... 544/71 |

FOREIGN PATENT DOCUMENTS

| 245020 | 11/1987 | European Pat. Off. . |
| 49-48631 | 12/1974 | Japan . |
| 55-36284 | 3/1980 | Japan . |
| 61-501145 | 6/1986 | Japan . |
| 1129869 | 5/1989 | Japan . |
| 1163184 | 6/1989 | Japan . |
| 4528892 | 9/1990 | Japan . |
| 3227988 | 10/1991 | Japan . |
| 4136085 | 5/1992 | Japan . |

OTHER PUBLICATIONS

Rickwood et al., Chemical Abstracts 121:257,914, 1994.
Nakamura et al, Chemical Abstracts 121:217,745, 1994.
Yamamoto et al., Chemical Abstracts 120:285,117, 1994.
Malatesta et al., Chemical Abstracts 117:251,299, 1992.
Yamamoto et al, Chemical Abstracts, 117:140,752, 1992.
Murayama et al., Chemical Abstracts, 116:83,683, 1992.
Rickwood et al., Chemical Abstracts 109:14,836, 1988.
Malatesta et al, Magnetic Resonance in Chemistry, 30, 905–913, 1992.

*Primary Examiner*—Matthew V. Grumbling
*Attorney, Agent, or Firm*—Sherman and Shalloway

[57] ABSTRACT

A spiro-naphtho-oxaine compound having a specific substituent providing red color development which has been unknown in the past, and photosensitive materials containing the compound. Since the compound is superior in fatigue resistance and has a sufficient red color developing density, it is used in plastic articles, optical filters, recording materials, textiles, decoration materials, and toys, which change in color by light irradiation to develop a magenta color.

24 Claims, No Drawings

SPIRO-NAPHTHO-OXAZINE COMPOUND AND PHOTOSENSITIVE MATERIALS USING THE SAME

FILED OF THE INVENTION

The present invention relates to a spiro-naphtho-oxazine compound having photochromatic characteristics, more specifically to photosensitive materials utilized in plastic articles, optical filters, recording materials, textiles, toys, and the like which are changed in color by irradiation with light.

DESCRIPTION OF PRIOR ART

Heretofore, spiro-naphtho-oxazine compounds have been known as photochromatic compounds. For example, Japanese Patent Publications 45-28892 and 49-48631, Japanese Patent Laid-open Publications (OPIs) 55-36284, 61-501145, 01-163184, 01-129869, 03-227988, 04-136085, and the like describe compounds of the following structures:

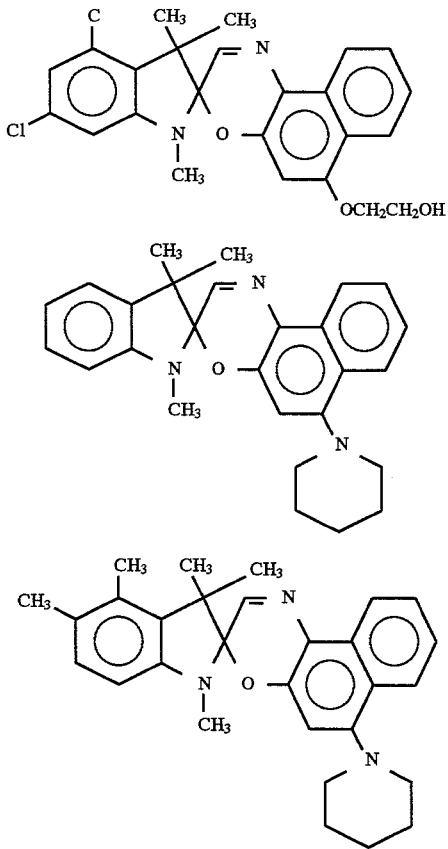

However, the known spiro-naphtho-oxazine compounds are known to be superior in light resistance, but the developed colors range from red-violet to blue-violet, and are thus insufficient in variety of hue. In particular, photochromatic photosensitive materials have been in demand which have peak absorption wavelengths of 500 to 560 mm when color-developed, are superior in fatigue resistance to repealed cycles of coloring arid de-coloring, and as magenta of the three primary colors.

SUMMARY OF THE INVENTION

The inventors have conducted intensive studies to solve these problems and found that a spiro-naphtho-oxazine compound having a specific substituent and photosensitive materials containing the compound are able to solve these problems, thus accomplishing the present invention. In accordance with the present invention, there is provided a spiro-naphtho-oxazine compound represented by the following general formula (1):

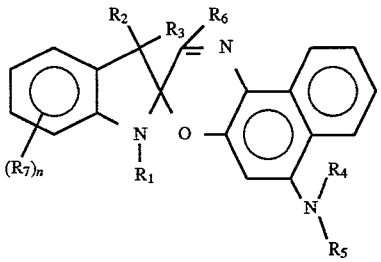

Formula (1)

(wherein, $R_1$ denotes a substituted or unsubstituted alkyl, a substituted or unsubstituted alkoxy, an alkoxyalkyl, a substituted or unsubstituted alkenyl, or a substituted or unsubstituted aryl; $R_2$ and $R_3$ independently denote alkyl, alkoxy, or alkoxyalkyl, or $R_2$ and $R_3$ may be linked to each other and cyclized; $R_4$ and $R_5$ independently denote hydrogen, alkoxy, or alkyl which may be substituted with hydroxy, or $R_4$ and $R_5$ may be linked to each other and cyclized to form a nitrogen-containing ring. $R_6$ denotes hydrogen or alkyl. $R_7$ are independent of each other, may be the same or different; and denote cyano, nitro, perfluoroalkyl, fluorine, chlorine, or bromine, n is an integer from 2 to 4) and photosensitive material containing the compound.

More specifically, $R_1$ includes alkyl; alkoxy; alkoxyalkyls such as methoxyethyl and ethoxyethyl; alkoxyalkoxyalkyls such as methoxyethoxyethyl and n-butoxyethoxyethyl; alkoxyalkoxyalkoxyalkyls such as methoxyethoxyethoxyethyl and ethoxyethoxyethoxyethyl; aryloxyalkyls which may be substituted such as phenyloxyethyl, naphthyloxyethyl, and p-chlorophenyloxyethyl; phenylalkyls which may be substituted such as benzyl, phenethyl, p-chlorobenzyl, and p-nitrobenzyl; cycloalkylalkyls such as cyclohexylmethyl, cyclohexylethyl, and cyclopentylmethyl; alkenyloxyalkyls which may be substituted such as allyloxyethyl and 3-bromoallyloxyethyl; cyanoalkyls such as cyanoethyl and cyanomethyl; hydroxyalkyls such as hydroxyethyl and hydroxymethyl; tetrahydrofurylalkyls such as tetrahydrofurfuryl and tetrahydrofurylethyl; substituted or unsubstituted thienylalkyls such as thienylethyl and thienylmethyl; substituted or unsubstituted alkenyls such as allyl and 2-chloroallyl; substituted or unsubstituted aryls such as phenyl, p-methylphenyl, naphthyl, and m-methoxyphenyl; or cycloalkyls such as cyclohexyl and cyclopentyl; and those which are substituted with cycloalkyls. Of these, $R_1$ is preferably alkyl of 1 to 6 carbon atoms, allyl, or phenyl.

$R_2$ and $R_3$ denote alkyls; alkoxys; and alkoxyalkyls such as methoxyethyl and ethoxyethyl, axed as $R_2$ and $R_3$, lower alkyls such as methyl, ethyl, propyl, and butyl, or cyclized $R_2$ and $R_3$ such as cyclohexyl are particularly preferable.

Practical examples of amino group substituted with $R_4$ and $R_5$ include the following:

Amino, methylamino, ethylamino, n-propylamino, n-butylamino, t-propylamino, t-butylamino, dimethylamino, diethylamino, di-n-propylamino, and di-n-butylamino, ethylmethylamino, n-propylmethylamino, n-butylethylamino, n-propyl (n-butyl) amino, hydroxyethylamino, methoxypopylamino, di-hydroxyethylamino, and methoxyethoxyethylamino.

Examples of $R_4$ and $R_5$ which are linked and cyclized to form nitrogen-containing heterocycles include the following:

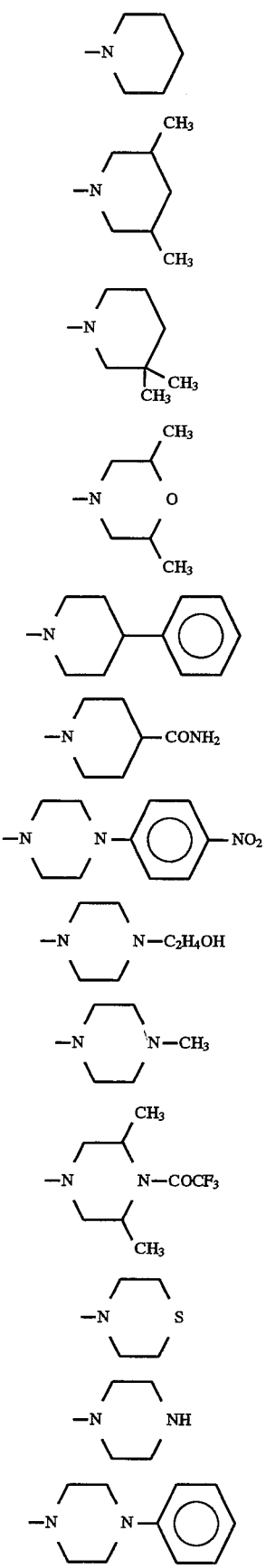

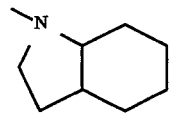
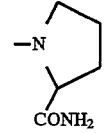
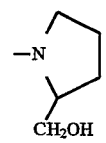
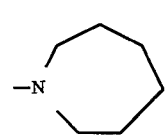

$R_6$ is preferably hydrogen or an electron donor such as alkyl.

$R_7$ preferably has a higher electron attractive property. The greater the value of the sum of the Hammett's substituent constants α which are parameters of electron donating and electron attracting properties of the substituent, the better objective red-coloring compound with superior fatigue resistance can be obtained.

Further, a dimer of the following general formula (2) obtained by replacing the substituent $R_1$ of the general formula (1) with alkylene, alkylene(polyoxy)alkylene, or alkylenearylalkylene is a photochromatic compound which develops a red color, is superior in fatigue resistance to repeated red coloring, and has a sufficient color developing density:

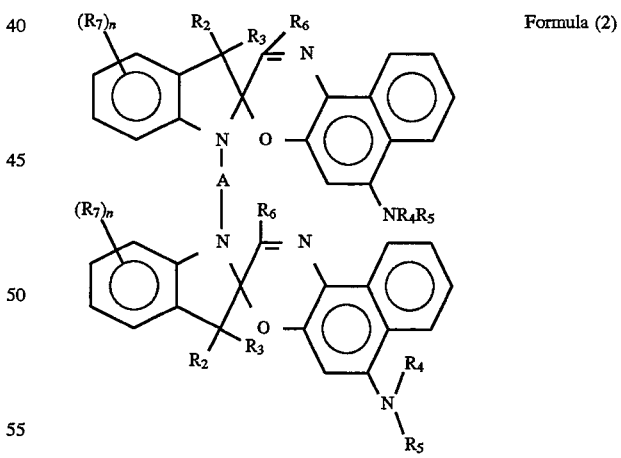

Formula (2)

(wherein, $R_2$, $R_3$, $R_4$, $R_5$, $R_6$, $R_7$ and n are as defined in the general formula (1)).

The spiro-naphtho-oxazine compound of the present invention can be synthesized by various methods. For example, it can be obtained by reacting an indolenine compound, an amine compound, and a nitrosonaphthol compound. The reaction solvent can be benzene, toluene, xylene, nitrobenzene, methanol, propanol, butanol, acetone, methylethylketone, dichloromethane, dichloroethane, trichloroethane, or the like. The reaction temperature is 0 to 200° C.

The photosensitive material of the present invention is prepared by a conventional method known in the art in which the spiro-naphtho-oxazine compound of the present invention is dissolved in a solvent and coated on a substrate, or, the compound is microencapsulated with gelatin or the like and mechanically adhered to a substrate, coated using a binder resin, kneaded with the binder resin, or homogeneously dispersed in a solvent or the like, or using a resin composition obtained by adding the inventive compound in the synthesis of the resin.

In the preparation of the photosensitive material, a hindered phenol type antioxidant, a hindered amine type antioxidant, or a stabilizer such as metal naphthenate may be added. The substrate can be one which does not impair coloring and de-coloring of the compound, such as paper, baryta paper, synthetic paper, fibers, synthetic resins, films, metal plates, glass, and the like. The binder resin is preferably one which does not impair coloring and de-coloring of the compound. Content of the inventive compound is 0.01 to 50 weight percent, preferably 0.1 to 30 weight percent, to the resin. Tile synthetic resin films and the binder resins can be polyethyleneglycol resin, polystyrene resin, polyvinylbutyral resin, polyvinyl chloride resin, polyvinylbutyral resin, polymethylmethacrylate resin, polyvinyl chloride resin, vinyl acetate copolymer resin, polycarbonate resin, styrene-butadiene copolymer resin, acrylic resin, epoxy resin, silicone resin, acetylcellulose resin, polyester resin, polyurethane resin, and the like, but are not limited thereto, and existing resins can also be used.

The organic solvent used can be benzene, toluene, xylene, tetrahydrofuran, acetone, methylethylketone, cyclohexane, acrylonitrile, methanol, ethanol, methylcellosolve, ethylcellosolve, ethyl acetate, dioxane, or the like. Further, mixtures thereof can also be preferably used.

A film-formed photosensitive layer can be formed on the substrate by a conventional method known in the art. Depending on the application as a photosensitive material, the film thickness is preferably 0.5 µm to 1.0 mm, and particularly a thickness of 5µ to 0.5 mm is preferable.

DETAILED DESCRIPTION OF THE PREFERRED EMBODIMENTS

The present invention will now be described in detail with reference to the practical synthetic examples and application examples as photosensitive materials, but the present invention is not limited to these examples.

EXAMPLE 1

Synthesis of compound (1)

1-Nitroso-2-naphthol in an amount of 13 g was dissolved in 200 ml of benzene, to which 13 g of piperidine was added, and stirred overnight at room temperature. Then, 19 g of 1,3,3-trimethyl-2-methylene-4,6-di (trifluoromethyl) indoline was added, and stirred at 60° C. for 3 hours. After completion of the reaction, the solvent was distilled out, by an evaporator, and the reaction product was separated and purified by silica gel column chromatography (solvent: benzene) to obtain 0.2 g of pale brown crystal represented by the following structural formula having a melting point of 166° to 167° C.

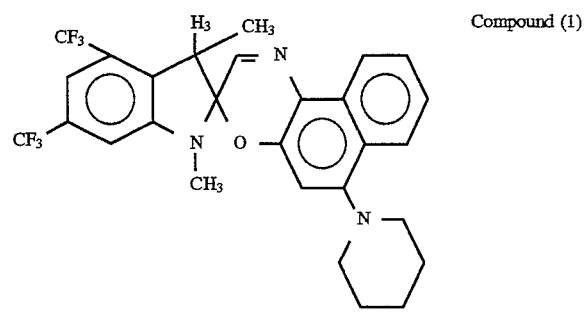

Compound (1)

Results of elementary analysis of the compound (1) were as shown below:

| Element | Theoretical value | (in %) Measured value |
| --- | --- | --- |
| C | 63.61 | 63.92 |
| H | 4.97 | 5.08 |
| F | 20.82 | 20.70 |
| N | 7.67 | 7.73 |

EXAMPLE 2

Synthesis of compound (2)

1-Nitroso-2-naphthol in an amount of 17 g was dissolved in 200 ml of benzene, to which 16 g of piperidine was added, and stirred overnight at room temperature. Then, 20 g of 1,3,3-trimethyl-2-methylene-4-trifluoromethyl-7-chloroindoline was added, and stirred at 60° C. for 3 hours. After completion of the reaction, the solvent was distilled out by an evaporator, and the reaction product was separated and purified by silica gel column chromatography (solvent: benzene) to obtain 0.5 g of pale yellow crystal represented by the following structural formula having a melting point of 174° to 175° C.

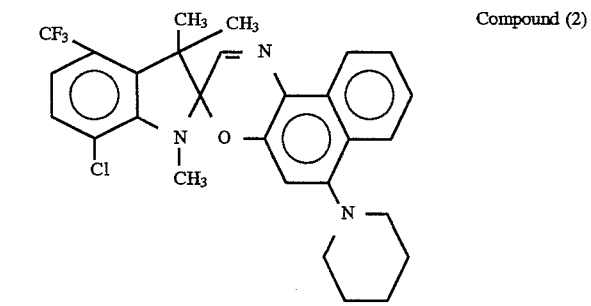

Compound (2)

Results of elementary analysis of the compound (2) were as shown below:

| Element | Theoretical value | (in %) Measured value |
| --- | --- | --- |
| C | 65.43 | 66.12 |
| H | 5.30 | 5.39 |
| N | 8.18 | 8.10 |
| F | 11.09 | 11.11 |
| Cl | 6.90 | 6.83 |

EXAMPLE 3

Synthesis of compound (3)

1-Nitroso-2-naphthol in an amount of 17 g was dissolved in 200 ml of benzene, to which 16 g of piperidine was added, and stirred overnight at room temperature. Then, 18 g of 1,3,3-trimethyl-2-methylene-5,6,7-trifluoroindoline was added, and stirred at 60° C. for 3 hours. After completion of the reaction, the solvent was distilled out by an evaporator, and the reaction product was separated and purified by silica gel column chromatography (solvent: benzene) to obtain 1.1 g of pale yellow crystal represented by the following structural formula having a melting point of 196° to 198° C.

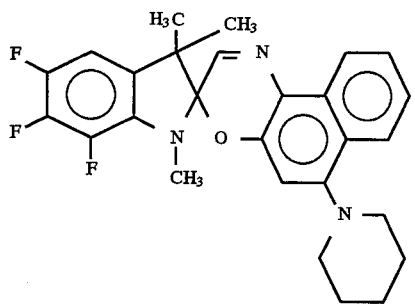

Compound (3)

Results of elementary analysis of the compound (3) were as shown below:

| Element | Theoretical value | (in %) Measured value |
|---|---|---|
| C | 69.66 | 68.25 |
| H | 5.63 | 5.71 |
| N | 9.03 | 8.98 |
| F | 12.24 | 12.10 |

EXAMPLE 4

Synthesis of compound (4)

1-Nitroso-2-naphthol in an amount of 14 g was dissolved in 200 ml of benzene, to which 13 g of piperidine was added, and stirred overnight at room temperature. Then, 18 g of 1,3,3-trimethyl-2-methylene-4,5,7-trichloroindoline was added, and stirred at 60° C. for 3 hours. After completion of the reaction, the solvent was distilled out by an evaporator, and the reaction product was separated and purified by silica gel column chromatography (solvent: benzene) to obtain 1.4 g of pale brown crystal represented by the following structural formula having a melting point of 201° to 202° C.

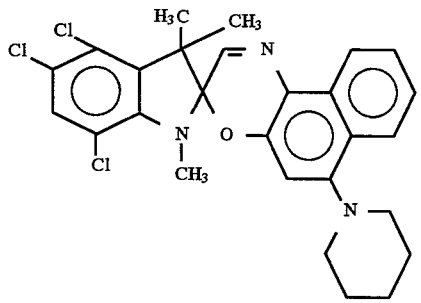

Compound (4)

Results of elementary analysis of the compound (4) were as shown below:

| Element | Theoretical value | (in %) Measured value |
|---|---|---|
| C | 62.98 | 62.87 |
| H | 5.09 | 5.13 |
| N | 8.16 | 8.20 |
| Cl | 20.66 | 20.76 |

Then, practical application examples of the photosensitive material will be described.

Application Example 1

The compound (1) in an amount of 10 g was dissolved in 3.3 g of a thermoplastic polyester resin (BYRON 200 (made by Toyobo Co. ): non-volatile content=30% by weight, MEK/toluene=2/8), coated oil art paper using a bar coater (winding wire diameter: 0.3 mm), and dried at 70° C. for 30 minutes to obtain a coated film. The photosensitive coated film surface was irradiated with a 9 W black light from a height of 3 cm at room temperature for 30 seconds. Immediately after the irradiation, the paper was measured for the maximum color developing wavelength by a color eye (made by Macbeth), and showed red color development of 544 nm. When the ultraviolet light source was removed, and the colored paper was allowed to stand for several hours or irradiated with visible light, the original colorless state was restored. This change could be repeatedly achieved.

Application Example 2

The compound (1) in an amount of 0.3% was added to a urethane resin, coated on art paper using a bar coater (winding wire diameter: 0.3 mm), and dried at 70° C. for 30 minutes to obtain a coated film. The photosensitive coated film surface was irradiated with a 9 W black light from a height of 3 cm at room temperature for 30 seconds. Immediately after the irradiation, the paper was measured for the maximum absorption wavelength by a color eye (made by Macbeth), and showed red color development of 544 nm. When the ultraviolet light source was removed, and the colored paper was allowed to stand for several hours or irradiated with visible light, the original colorless state was restored. This change could be repeatedly achieved.

Application Example 3

The compound (1) in an amount of 0.1% was added to a polystyrene resin to obtain a coated film. The photosensitive coated film surface was irradiated with an 80 W high pressure mercury lamp from a height of 10 cm at room temperature for 2 seconds. Immediately after the irradiation, the paper was measured for the maximum absorption wavelength by a color eye (made by Macbeth), and showed red color development of 548 nm. When the ultraviolet light source was removed, and the colored film was allowed to stand for several hours or irradiated with visible light, the original colorless state was restored. This change could be repeatedly achieved.

Application Example 4

The compound (1) in an amount of 0.1% was added to an acrylic resin to obtain a coated film. The photosensitive coated film surface was irradiated with an 80 W high-pressure mercury lamp from a distance of 10 cm for 2 seconds. Immediately after the irradiation, the film was measured for the maximum absorption wavelength by a color eye (made by Macbeth), and showed red color development of 543 nm. When the ultraviolet light source was removed, and the colored film was allowed to stand for several hours or irradiated with visible light, the original colorless state was restored. This change could be repeatedly achieved.

Application Example 5

The compound (1) in an amount of 1.4 g was dissolved in 50 g of an oil of alkyl naphthalene (KMC113 (made by Kureha Chemical) at 94° C., cooled to room temperature, 70 g of 5% by weight Scripset #520, and emulsified by a homomixer for 15 minutes to obtain an emulsion. Then, a mixture of 6 g of melamine, 17 g of formaldehyde, and 37 g of water was adjusted to pH9 with 5% by weight aqueous NaOH solution, stirred at 60° C. for 30 minutes, to which all of the emulsion was added, and stirred at 80° C. for 90 minutes. After cooling to room temperature, the reaction liquid was readjusted to pH9 with 5% by weight aqueous NaOH solution. The resulting microcapsule slurry was filtered, washed with water, and dried to obtain 2 to 10 μm melamine resin microcapsules containing the compound (1). When the microcapsules were exposed to outdoor sunlight, they were changed to a red color. When the microcapsules were returned indoors, the color was reverted back to white.

Application Example 6

The same procedure as in Application Example 5 was used, except that dioctyl phthalate was used in place of KMC113, to obtain 2 to 10μm microcapsules. When the microcapsules were exposed to outdoor sunlight, they were changed to a red color. When the microcapsules were returned indoors, the color was reverted back to white.

Using various types of spiro-naphtho-oxazine compounds synthesized using the same procedure as in Synthesis Example of the compound (1), photosensitive coating films were formed on art paper using the same procedure as in Application Example 1, irradiated with ultraviolet, light by a black light, and measured for the maximum absorption wavelength (λmax). The results are shown in Tables 1 and 2.

$R_1$ to $R_7$ and A in Tables 1 and 2 denote the individual substituents in the following general formulae (1) and (2).

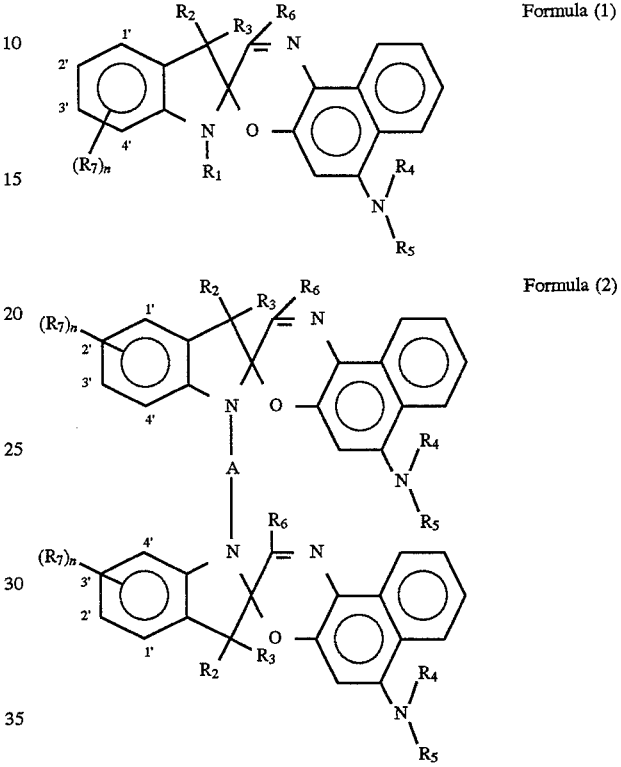

Formula (1)

Formula (2)

| Example | $R_1$ or A (dimer) | $R_2$ $R_3$ | $-N\begin{smallmatrix}R_4\\R_5\end{smallmatrix}$ | $R_6$ | $(R_7)_n$ | Color development in UV irradiation Color | λmax (nm) |
|---|---|---|---|---|---|---|---|
| 2 | —CH$_3$ | —CH$_3$ —CH$_3$ | —N(piperidine) | H | 1'-CF$_3$, 4'-Cl | Red | 548 |
| 3 | —CH$_3$ | —CH$_3$ —CH$_3$ | —N(piperidine) | H | 2'-F, 3'-F, 4'-F | Red | 550 |
| 4 | —CH$_3$ | —CH$_3$ —CH$_3$ | —N(piperidine) | H | 1'-Cl, 2'-Cl, 4'-Cl | Red | 550 |
| 5 | —CH$_3$ | —CH$_3$ —CH$_3$ | —N(decahydroquinoline) | H | 1'-Cl, 2'-Cl, 4'-Cl | Red | 548 |
| 6 | —C$_2$H$_4$OC$_7$H$_{15}$(n) | —CH$_3$ —CH$_3$ | —N(piperazine)N—OCOCH$_3$ | H | 1'-Cl, 2'-Cl, 4'-Cl | Red | 549 |

-continued

| Example | R₁ or A (dimer) | R₂ R₃ | $-N\begin{smallmatrix}R_4\\R_5\end{smallmatrix}$ | R₆ | (R₇)ₙ | Color development in UV irradiation | |
|---|---|---|---|---|---|---|---|
| | | | | | | Color | λmax (nm) |
| 7 | —(CH₂)₄—O—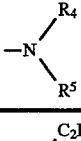 | —CH₃<br>—CH₃ | —N(C₂H₅)₂ 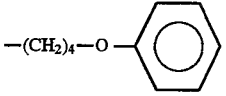 | CH₃ | 2'-NO₂, 4'-Cl | Red | 543 |
| 8 | —CH₂—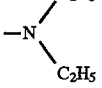 | —C₂H₅<br>—C₂H₅ | 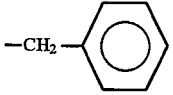 (morpholine) | CH₃ | 2'-NO₂, 4'-CN | Red | 540 |
| 9 | —C₁₈H₃₇(n) | 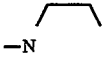 |  (thiomorpholine) | H | 1'-CF₃, 3'-CF₃ | Red | 543 |
| 10 | —CH₂—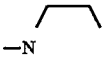—CH₂— (dimer) | —C₃H₇(n)<br>—C₃H₇(n) | 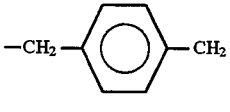 (4-methylpiperidine) | H | 1'-Br, 2'-Br, 4'-Br | Red | 556 |
| 11 | —C₂H₅ | —C₂H₅<br>—C₂H₅ | 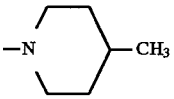 (4-phenylpiperidine) | CH₃ | 1'-CF₃, 4'-F | Red | 543 |
| 12 | —C₂H₅ | 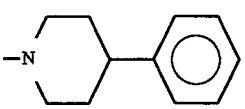 |  (4-carbamoylpiperazine) | H | 1'-C₂F₅, 4'-Cl | Red | 550 |
| 13 | 1,6-Hexanediyl (dimer) | —C₂H₅<br>—C₂H₅ | —N(C₂H₄OH)₂ | H | 2'-Cl, 4'-F | Red | 558 |

| Comparative Example | R₁ or A (dimer) | R₂ R₃ | —NR₄R₅ | R₆ | Substituent corresponding to R₇ | Color development in UV irradiation | |
|---|---|---|---|---|---|---|---|
| | | | | | | Color | λmax (nm) |
| 1 | —CH₃ | —CH₃<br>—CH₃ | 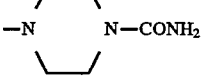 (piperidine) | H | No substituent | Purple | 575 |
| 2 | —CH₃ | —CH₃<br>—CH₃ |  (piperidine) | H | 2'-OCH₃ | Bule | 600 |
| 3 | —CH₃ | —CH₃<br>—CH₃ |  (decahydroquinoline) | H | No substituent | Purple | 570 |
| 4 | —CH₃ | —CH₃<br>—CH₃ | —N(C₂H₅)₂ | H | 2'-F | Purple | 575 |
| 5 | —CH₂— (2,4-dichlorobenzyl) | —CH₃<br>—CH₃ | —N(C₂H₅)₂ | H | 2'-Cl | Purple | 570 |

-continued

| Comparative Example | R₁ or A (dimer) | R₂ R₃ | —NR₄R₅ | R₆ | Substituent corresponding to R₇ | Color development in UV irradiation Color | λmax (nm) |
|---|---|---|---|---|---|---|---|
| 6 | —C₂H₄OC₇H₁₅(n) | —CH₃ —CH₃ | —N(piperidinyl) | H | 2'-CH₃ | Purple | 582 |
| 7 | —(CH₂)₄—O—phenyl | —CH₃ —CH₃ | —N(piperidinyl) | H | 2'-CH₃ | Purple | 581 |
| 8 | —C₁₈H₃₇(n) | —CH₃ —CH₃ | —N(2,6-dimethylpiperazinyl)—COCF₃ | CH₃ | 2'-Cl | Purple | 575 |
| 9 | —CH₂—phenyl—CH₂— (dimer) | cyclohexyl | —N(piperidinyl)—CONH₂ | CH₃ | 2'-Br | Purple | 580 |
| 10 | 1,6-Hexanediyl (dimer) | —C₂H₅ —C₂H₅ | —N(4-phenylpiperidinyl) | CH₃ | 2'-F | Purple | 576 |

We claim:

1. A spiro-naphtho-oxazine compound represented by the formula (1):

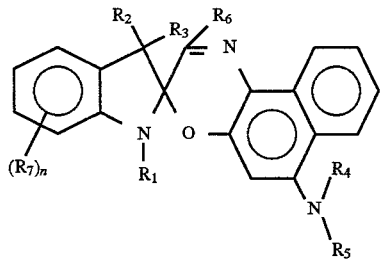

Formula (1)

wherein, $R_1$ denotes a substituted or unsubstituted alkyl, a substituted or unsubstituted alkoxy, an alkoxyalkyl, a substituted or unsubstituted alkenyl, or a substituted or unsubstituted aryl; $R_2$ and $R_3$ independently denote alkyl, alkoxy, or alkoxyalkyl, or $R_2$ and $R_3$ may be linked to each other to form a five or six member carbon ring, or a five or a six member ring containing carbon and oxygen; $R_4$ and $R_5$ independently denote hydrogen, alkoxy, or alkyl which may be substituted with hydroxy, or $R_4$ and $R_5$ may be linked to each other, to form a five or six member ring containing carbon and nitrogen or a five or six member ring containing carbon and nitrogen and either oxygen or sulfur, $R_6$ denotes hydrogen or alkyl, and $R_7$ are independent of each other, may be the same or different, and denote perfluoroloweralkyl, fluorine or chlorine and n is an integer from 2 to 4, and at least one $R_7$ is fluorine or perfluoroloweralkyl.

2. A spiro-naphtho-oxazine compound represented by the formula (2):

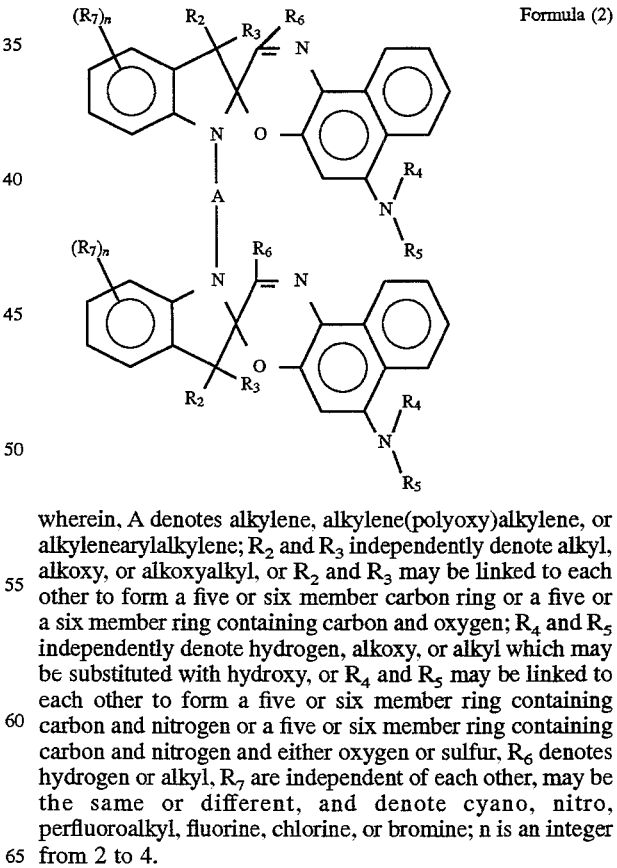

Formula (2)

wherein, A denotes alkylene, alkylene(polyoxy)alkylene, or alkylenearylalkylene; $R_2$ and $R_3$ independently denote alkyl, alkoxy, or alkoxyalkyl, or $R_2$ and $R_3$ may be linked to each other to form a five or six member carbon ring or a five or a six member ring containing carbon and oxygen; $R_4$ and $R_5$ independently denote hydrogen, alkoxy, or alkyl which may be substituted with hydroxy, or $R_4$ and $R_5$ may be linked to each other to form a five or six member ring containing carbon and nitrogen or a five or six member ring containing carbon and nitrogen and either oxygen or sulfur, $R_6$ denotes hydrogen or alkyl, $R_7$ are independent of each other, may be the same or different, and denote cyano, nitro, perfluoroalkyl, fluorine, chlorine, or bromine; n is an integer from 2 to 4.

3. A photosensitive material containing the spiro-naphtho oxazine compound of claim 1.

4. A photosensitive material containing the spiro-naphtho-oxazine compound of claim 2.

5. The spiro-naphtho-oxazine compound of claim 1, which when irradiated shows a red color.

6. The spiro-naphtho-oxazine compound of claim 1, wherein $R_7$ are independent of each other, and one denotes chlorine, fluorine or perfluoroalkyl and another denotes fluorine or perfluoroalkyl.

7. The spiro-naphtho-oxazine compound of claim 1, wherein $R_1$ is —$C_{18}H_{37}$, $R_2$ and $R_3$ are cyclohexyl, $R_4$ and $R_5$ are

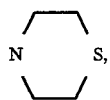

$R_6$ is hydrogen and $R_7$ are 1'—$CF_3$ and 3'—$CF_3$.

8. The spiro-naphtho-oxazine compound of claim 2, which when irradiated shows a red color.

9. The spiro-naphtho-oxazine compound of claim 2, wherein $R_7$ are independent of each other, and one denotes chlorine, fluorine or perfluoroalkyl and another denotes fluorine or perfluoroalkyl.

10. The spiro-naphtho-oxazine compound of claim 2, wherein A is —$CH_2C_2$-,

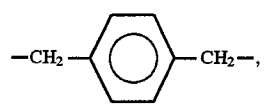

$R_2$ and $R_3$ are each $C_3H_7$, $R_4$ and $R_5$ are

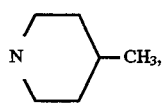

$R_6$ is hydrogen and $R_7$ are 1'—Br, 2'—Br and 4'—Br.

11. The spiro-napto-oxazine compound of claim 2, wherein A is 1,6-Hexanedily, $R_2$ and $R_3$ are each -$CH_2H_5$, $R_4$ and $R_5$ are —$N(C_2H_4OH)_2$, $R_6$ is H, and $R_7$ are 2'—Cl and 4'—F.

12. A spiro-naphtho-oxazine compound represented by the formula (1):

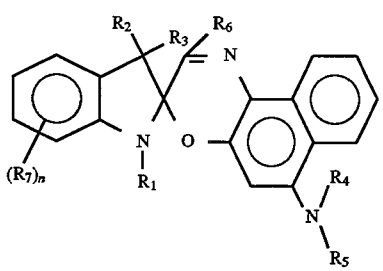

Formula (1)

wherein, $R_1$ denotes a $C_{1-6}$ alkyl, allyl or phenyl; $R_2$ and $R_3$ independently denote $C_1$ to $C_4$ alkyl, or $R_2$ and $R_3$ may be linked to each other to form cyclohexyl; $R_4$ and $R_5$ independently denote hydrogen, or $C_1$ to $C_4$ alkyl, or $R_4$ and $R_5$ may be linked to each other to form a carbon and nitrogen-containing six member ring, $R_6$ denotes hydrogen or lower alkyl, and $R_7$ are independent of each other, may be the same or different, and denote perfluoroloweralkyl, fluorine or chlorine, and n is an integer from 2 to 4, and at least one $R_7$ is fluorine or perflouroloweralkyl and which when irradiated shows a red color.

13. The spiro-naphtho-oxazine compound of claim 12, wherein $R_7$ are independent of each other, and one denotes chlorine, fluorine or perflouroloweralkyl and another denotes fluorine or perflouroloweralkyl.

14. The spiro-naphtho-oxazine compound of claim 12, wherein $R_1$ is —$CH_3$, $R_2$ and $R_3$ are each $CH_3$, $R_4$ and $R_5$ are N

$R_6$ is hydrogen and $R_7$ are 1'—$CF_3$ and 3'$CF_3$.

15. The spiro-naphtho-oxazine compound of claim 12, wherein R is —$CH_3$, $R_2$ and $R_3$ are each —$CH_3$, $R_4$ and $R_5$ are

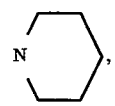

$R_6$ is hydrogen and $R_7$ are 1'—$CF_3$ and 4'—Cl.

16. The spiro-naphtho-oxazine compound of claim 12, wherein $R_1$ is —$CH_3$, $R_2$ and $R_3$ are each —$CH_3$ $R_4$ and $R_5$ are

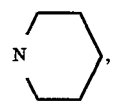

$R_6$ is hydrogen and $R_7$ are 2'—F, 3'—F and 4'—F.

17. The spiro-naphtho-oxazine compound of claim 12, wherein $R_1$ is —$CH_2H_5$, and $R_2$ and $R_3$ are each $C_2H_5$, $R_4$ and $R_5$ are

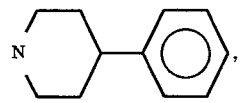

$R_6$ is $CH_3$ and $R_7$ are 1'$CF_3$ and 4'—F.

18. The spiro-naphtho-oxazine compound of claim 12, wherein R is $C_2H_5$, $R_2$ and $R_3$ are cyclohexyl, $R_4$ and $R_5$ are

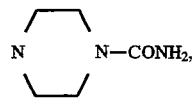

$R_6$ is hydrogen and $R_7$ are 1'—$C_2F_5$ and 4'Cl.

19. A photosensitive material comprising the spiro-naphtho-oxazine compound of claim 12 in an amount of 0.1 to 30% by weight and a resin carrier or binder.

20. A spiro-naphtho-oxazine compound represented by the formula (2):

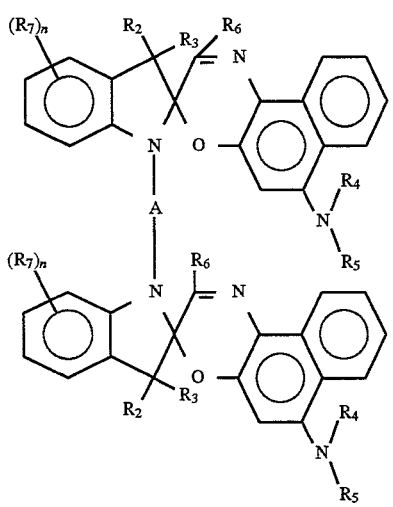

Formula (2)

wherein, A denotes lower alkylene, or lower alkylenearylalkylene; $R_2$ and $R_3$ independently denote $C_1$–$C_4$ alkyl, or $R_2$ and $R_3$ may be linked to each other to form cyclohexyl; $R_4$ and $R_5$ independently denote hydrogen or $C_1$ to $C_4$ alkyl, or $R_4$ and $R_5$ may be linked to each other to form a carbon and nitrogen-containing six member ring, $R_6$ denotes hydrogen or lower alkyl, and $R_7$ are independent of each other, may be the same or different, and denote perfluoroloweralkyl, fluorine or chlorine and n is an integer from 2 to 4, and which when irradiated shows a red color.

21. The spiro-naphtho-oxazine compound of 20, wherein $R_7$ are independent of each other, and one denotes chlorine, fluorine or perflouroloweralky and another other denotes fluorine or perflouroloweralkyl.

22. A photosensitive material comprising the spiro-naphtho-oxazine compound of claim 20 in an amount of 0.1 to 30% by weight and a resin carrier or binder.

23. The spiro-naphtho-oxazine compound of claim 1 wherein $R_2$ and $R_3$ may be linked to each other to form a five or six member carbon ring, and $R_4$ and $R_5$ may be linked to each other to form a five or six member ring containing carbon and nitrogen.

24. The spiro-naphtho-oxazine compound of claim 2 wherein $R_2$ and $R_3$ may be linked to each other to form a five or six member carbon ring, and $R_4$ and $R_s$ may be linked to each other to form a five or six member ring containing carbon and nitrogen.

* * * * *